US 11,253,304 B2

(12) United States Patent
Lee et al.

(10) Patent No.: US 11,253,304 B2
(45) Date of Patent: Feb. 22, 2022

(54) HYBRID CANNULATED ORTHOPEDIC SCREWS

(71) Applicant: GLW, Inc., Waxhaw, NC (US)

(72) Inventors: Thomas Hoon Lee, Columbus, OH (US); Axel Cremer, Fahrenkrug (DE); Klaus Dorawa, Kiel (DE); Christian Lutz, Heikendorf (DE); Stefan Völzow, Mönkeberg (DE); Lowell Weil, Jr., Lake Forest, IL (US)

(73) Assignee: GLW, Inc., Englewood Cliffs, NJ (US)

( * ) Notice: Subject to any disclaimer, the term of this patent is extended or adjusted under 35 U.S.C. 154(b) by 115 days.

(21) Appl. No.: 16/238,791

(22) Filed: Jan. 3, 2019

(65) Prior Publication Data
US 2019/0209220 A1    Jul. 11, 2019

Related U.S. Application Data

(60) Provisional application No. 62/613,186, filed on Jan. 3, 2018.

(51) Int. Cl.
*A61B 17/86* (2006.01)
*A61B 17/84* (2006.01)

(52) U.S. Cl.
CPC ........ *A61B 17/8635* (2013.01); *A61B 17/846* (2013.01); *A61B 17/863* (2013.01);
(Continued)

(58) Field of Classification Search
CPC . A61B 17/8635; A61B 17/846; A61B 17/863; A61B 17/869; A61B 17/8605;
(Continued)

(56) References Cited

U.S. PATENT DOCUMENTS

| 4,280,233 A | 7/1981 | Raab |
| 4,338,926 A | 7/1982 | Kummer et al. |

(Continued)

FOREIGN PATENT DOCUMENTS

| CN | 101128157 | 2/2008 |
| CN | 101426444 | 5/2009 |

(Continued)

OTHER PUBLICATIONS

European Patent Office. "International Search Report and Written Opinion" for PCT application No. PCT/US2019/012142. dated Mar. 29, 2019. pp. 1-10.

(Continued)

*Primary Examiner* — Kevin T Truong
*Assistant Examiner* — Tracy L Kamikawa
(74) *Attorney, Agent, or Firm* — MacMillan, Sobanski & Todd, LLC

(57) ABSTRACT

The disclosure relates to medical devices and methods of manufacturing medical devices. An orthopedic screw includes an inner core member having a head having a first outer diameter, a tip having a second outer diameter, and a body extending between the head and the tip and having a third outer diameter that is less than the first outer diameter and the second outer diameter. An outer body member is disposed circumferentially around the body of the inner core member and defines an outer body member external thread. The tip of the inner core member can define an inner core member external thread that forms an interrupted thread with the outer body member external thread.

17 Claims, 11 Drawing Sheets

(52) U.S. Cl.
    CPC ........ *A61B 17/8685* (2013.01); *A61B 17/864* (2013.01); *A61B 17/8605* (2013.01); *A61B 17/866* (2013.01); *A61B 17/869* (2013.01)

(58) Field of Classification Search
    CPC . A61B 17/866; A61B 17/864; A61B 17/8685; A61B 17/8625
    See application file for complete search history.

(56) References Cited

U.S. PATENT DOCUMENTS

| | | | |
|---|---|---|---|
| 5,571,139 | A | 11/1996 | Jenkins, Jr. |
| 7,033,398 | B2 | 4/2006 | Graham |
| 7,850,690 | B2 | 12/2010 | Frigg et al. |
| 7,850,717 | B2 * | 12/2010 | Dewey ............... A61B 17/7001 606/246 |
| 8,092,505 | B2 | 1/2012 | Sommers |
| 8,454,606 | B2 | 6/2013 | Frigg et al. |
| 8,608,743 | B2 * | 12/2013 | Baumgartner ............ A61F 2/28 606/76 |
| 8,663,224 | B2 | 3/2014 | Overes et al. |
| 8,702,767 | B2 | 4/2014 | Nebosky et al. |
| 8,709,055 | B2 | 4/2014 | Beyar et al. |
| 8,784,430 | B2 | 7/2014 | Kay et al. |
| 8,979,865 | B2 | 3/2015 | Fan et al. |
| 8,998,987 | B2 | 4/2015 | Wallick |
| 9,101,417 | B2 | 8/2015 | Beyar et al. |
| 9,174,390 | B2 | 11/2015 | Lechmann et al. |
| 9,440,379 | B2 | 9/2016 | Smith et al. |
| 9,452,001 | B2 | 9/2016 | Faccioli et al. |
| 9,492,210 | B2 | 11/2016 | Rains et al. |
| 9,770,273 | B2 | 9/2017 | Guitelman |
| 10,022,164 | B2 | 7/2018 | Mangiardi |
| 10,022,165 | B2 | 7/2018 | Mangiardi |
| 10,028,777 | B2 | 7/2018 | Beyar et al. |
| 2006/0247638 | A1 | 11/2006 | Trieu et al. |
| 2007/0049938 | A1 | 3/2007 | Wallace et al. |
| 2007/0049939 | A1 | 3/2007 | Wallace et al. |
| 2007/0049940 | A1 | 3/2007 | Wallace et al. |
| 2007/0233071 | A1 | 10/2007 | Dewey et al. |
| 2009/0018590 | A1 | 1/2009 | Dorawa et al. |
| 2009/0043307 | A1 | 2/2009 | Faccioli et al. |
| 2010/0114097 | A1 | 5/2010 | Siravo et al. |
| 2010/0211118 | A1 * | 8/2010 | Christen ............ A61B 17/8635 606/312 |
| 2010/0228301 | A1 * | 9/2010 | Greenhalgh ....... A61B 17/8685 606/313 |
| 2011/0093020 | A1 | 4/2011 | Wu |
| 2011/0208189 | A1 | 8/2011 | Faccioli et al. |
| 2011/0245832 | A1 | 10/2011 | Giersch et al. |
| 2011/0257689 | A1 * | 10/2011 | Fiechter ............... A61B 17/866 606/301 |
| 2012/0271361 | A1 | 10/2012 | Zhou et al. |
| 2014/0105776 | A1 | 4/2014 | Ellero et al. |
| 2014/0188113 | A1 | 7/2014 | Overes et al. |
| 2014/0371799 | A1 * | 12/2014 | Sixto ..................... A61B 50/36 606/281 |
| 2017/0105774 | A1 * | 4/2017 | Prien ................... A61B 17/861 |
| 2017/0105776 | A1 | 4/2017 | Lutz |
| 2019/0053836 | A1 | 2/2019 | Sweeney et al. |
| 2019/0151000 | A1 * | 5/2019 | Kane ................. A61B 17/8635 |
| 2019/0216513 | A1 | 7/2019 | Sands et al. |

FOREIGN PATENT DOCUMENTS

| | | |
|---|---|---|
| CN | 101686844 | 3/2010 |
| CN | 102355863 | 2/2012 |
| CN | 102008751 | 1/2014 |
| EP | 1265653 | 6/2004 |
| JP | H07213534 | 8/1995 |
| WO | WO2001074262 | 10/2001 |
| WO | WO2004024012 | 3/2004 |
| WO | WO2007101267 | 9/2007 |
| WO | WO2008134264 | 11/2008 |
| WO | WO2011066522 | 6/2011 |
| WO | WO2011082152 | 7/2011 |
| WO | WO20120065068 | 5/2012 |
| WO | WO2014152262 | 1/2014 |
| WO | WO2015137911 | 9/2015 |
| WO | WO2015172842 | 11/2015 |
| WO | WO2016125054 | 8/2016 |

OTHER PUBLICATIONS

Patent Office of the China State Intellectual Property Office, First Office Action dated Feb. 5, 2018, pp. 1-8.

* cited by examiner

HYBRID CANNULATED ORTHOPEDIC SCREWS

CROSS-REFERENCE TO RELATED APPLICATIONS

This application claims benefit to the U.S. Provisional Patent Application No. 62/613,186, filed Jan. 3, 2018, which is incorporated by reference into this disclosure in its entirety.

FIELD

The disclosure relates to the field of medical devices. More particularly, the disclosure relates to implantable medical devices useful for orthopedic applications. Specific examples relate to orthopedic screws. The disclosure also relates to methods of manufacturing a medical device, including methods of manufacturing an orthopedic screw.

BACKGROUND

Orthopedic screws, also referred to as bone screws, are implantabled medical devices that are commonly used for fracture stabilization and fixation. These devices can be made from a variety of materials and can include structural adaptations that facilitate their use and/or enhance their performance. For example, some orthopedic screws define a cannula to enable placement over a wire.

While hybrid orthopedic screws are known, the inclusion of multiple materials in the construction of an orthopedic screw typically results in handling and performance drawbacks.

A need remains, therefore, for improved hybrid orthopedic screws.

BRIEF SUMMARY OF SELECTED EXAMPLES

Various example medical devices are described, including example orthopedic screws.

An example orthopedic screw comprises an inner core member having a head having a first outer diameter, a tip having a second outer diameter, and a body extending between the head and the tip and having a third outer diameter that is less than the first outer diameter and the second outer diameter. An outer body member is disposed circumferentially around the body of the inner core member and defines an outer body member external thread.

Another example orthopedic screw comprises an inner core member having a head having a first outer diameter, a tip having a second outer diameter, and a body extending between the head and the tip and having a third outer diameter that is less than the first outer diameter and the second outer diameter. The tip defines an inner core member external thread. An outer body member is disposed circumferentially around the body of the inner core member and defines an outer body member external thread. The inner core member external thread and the outer body member external thread form an interrupted thread.

Another example orthopedic screw comprises an inner core member having a proximal end defining a circumferential flange, a head having a first outer diameter, a tip having a second outer diameter, and a body extending between the head and the tip and defining a circumferential recess having a third outer diameter that is less than the first outer diameter and the second outer diameter. The tip defines an inner core member external thread having a first flange width. An outer body member is disposed circumferentially around the body of the inner core member and within the circumferential recess. The outer body member defines an outer body member external thread having a second flange width that is less than the first flange width. The inner core member external thread and the outer body member external thread form an interrupted thread.

Various example methods of manufacturing an orthopedic screw are described.

An example method of manufacturing an orthopedic screw comprises machining an inner core member from a precursor; placing the inner core member into a mold, and overmolding the inner core member with a material to form an outer body member about the inner core member to produce an orthopedic screw according to an embodiment.

Additional understanding of the claimed devices and methods can be obtained by reviewing the detailed description of selected examples, below, with reference to the appended drawings.

DETAILED DESCRIPTION OF SELECTED EXAMPLES

The following detailed description and the appended drawings describe and illustrate various example medical devices and methods. The description and illustration of these examples enable one skilled in the art to make and use examples of the inventive medical devices and to perform examples of the inventive methods. They do not limit the scope of the claims in any manner.

As used herein, the term "lumen," and grammatically related terms, refers to the inside space of a tubular structure. The term does not require any specific dimensions, relative dimensions, configuration, or regularity.

As used herein, the term "circumferential," and grammatically related terms, refers to a structural arrangement of one structure relative to another structure, feature, or property of another structure. The term does not require any specific dimensions, relative dimensions, configuration, or regularity of either structure.

Figure 1:
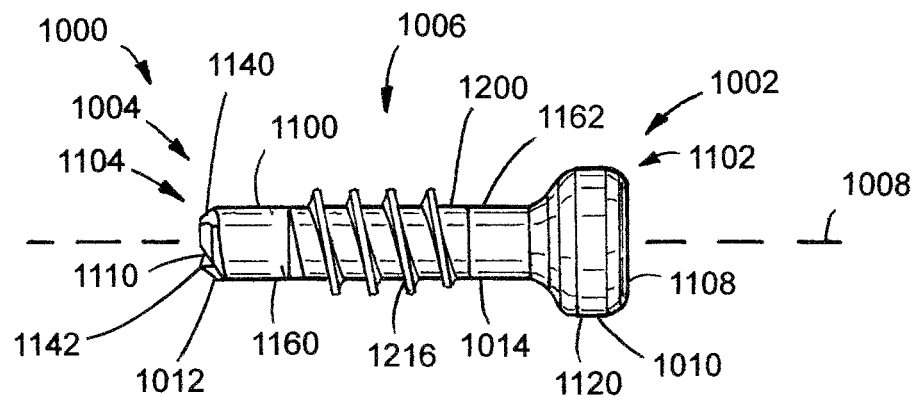
FIG. 1 is a side view of a first example orthopedic screw.
Figure 2:
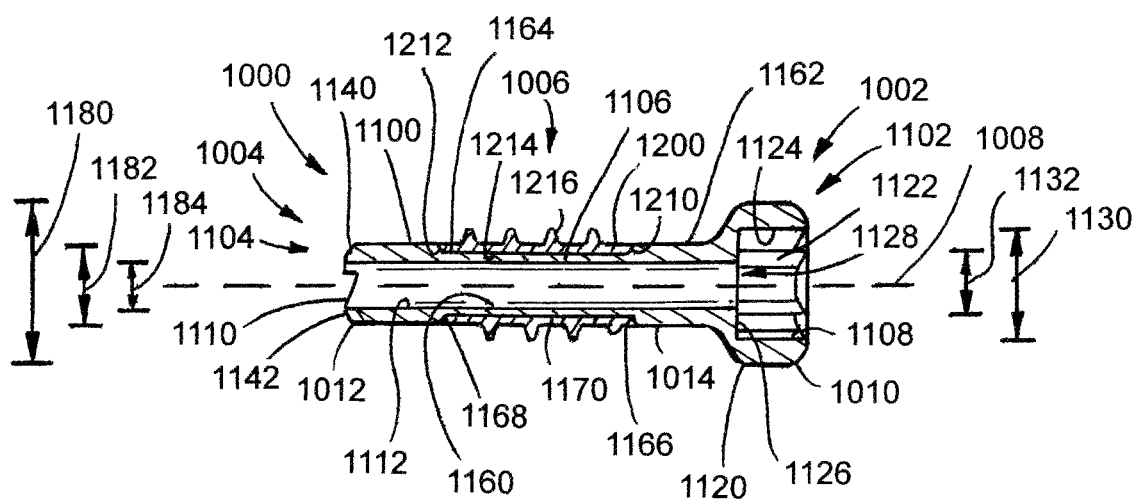
FIG. 2 is longitudinal cross-sectional view of the first example orthopedic screw.

FIGS. 1 and 2 illustrate a first example orthopedic screw 1000. The orthopedic screw 1000 has a proximal end 1002, a distal end 1004, and a body 1006 extending between the proximal end 1002 and the distal end 1004 along a longitudinal axis 1008. The orthopedic screw 1000 includes a head portion 1010 located at the proximal end 1002, a tip portion 1012 located at the distal end 1004, and a shaft 1014 extending between the head portion 1010 and the tip portion 1012 and comprising the body 1006. As described in detail below, the tip portion 1012 provides structure for cutting into tissue, such as bone and/or cartilage, and the head portion 1010 provides structure for interacting with one or more tools for placing or implanting the orthopedic screw 1000 into tissue, such as a driver. The orthopedic screw 1000 includes an inner core member 1100 and an outer body member 1200 disposed circumferentially around a portion of the inner core member 1100. Also as described in detail below, the orthopedic screw 1000 is a cannulated screw, allowing it to be passed over a separate member, such as a wire, to facilitate placement and/or positioning during implantation.

The inner core member 1100 has a proximal end 1102, a distal end 1104, and a body 1106 extending between the proximal end 1102 and the distal end 1104. The proximal end 1102 defines a proximal opening 1108 and the distal end 1104 defines a distal opening 1110. As best illustrated in FIG. 2, the inner core member 1100 defines a lumen 1112 extending between the proximal opening 1108 and the distal opening 1110. Thus, each of the proximal opening 1108 and the distal opening 1110 provides access to the lumen 1112 from the environment external to the orthopedic screw 1000. In use, the orthopedic screw 1000 can be passed over a previously-placed wire such that the wire extends through the lumen 1112. The orthopedic screw 1000 can then be advanced over the wire to achieve a desired placement and/or positioning before initiating driving of the orthopedic screw 1000 into tissue.

The inner core member 1100 defines a head 1120 at the proximal end 1102, a tip 1140 at the distal end 1104, and a body 1160 extending between the head 1120 and the tip 1140 along the longitudinal axis 1108 of the orthopedic screw 1008. The head 1120 defines a cavity 1122 that is bounded by a circumferential wall 1124 and a transverse wall 1126. The circumferential wall 1124 surrounds the longitudinal axis 1008 of the orthopedic screw 1000. The transverse wall 1126 defines inner opening 1128 that transitions the inner diameter of the lumen 1112 from the larger inner diameter 1130 of the cavity 1122 to the smaller inner diameter 1132 of the body 1106 of the inner core member 1100.

The circumferential wall 1124 defines structure that facilitates interaction with a tool, such as a driver, that can be used to implant drive the orthopedic screw 1000 into tissue, such as cartilage and/or bone. The transverse wall 1126 may also define structure that facilitates such interaction. As such, the circumferential wall 1124, the transverse wall 1126, and, as a result, the cavity 1122 may have any suitable configuration and a skilled artisan will be able to select an appropriate configuration for each of these structures in an orthopedic screw according to a particular embodiment based on various considerations, including the configuration and nature of any driver with which the orthopedic screw is intended to be used. Examples of suitable configurations include conventional configurations for screw heads, including hex-shaped configurations, star-shaped configurations, such as configurations compatible with TORX brand drivers, and other configurations. In this example, the head 1120 is an enlarged structure relative to the tip 1140 and body 1160 of the inner core member 1100.

The tip 1140 is positioned at the distal end 1104 of the inner core member 1100 and defines cutting edge 1142. Cutting edge 1142 defines structure for cutting into tissue, such as bone and/or cartilage. Cutting edge 1142 may have any suitable configuration and a skilled artisan will be able to select an appropriate configuration for the cutting edge in an orthopedic screw according to a particular embodiment based on various considerations, including the nature of any particular tissue with which the orthopedic screw is intended to be used. Examples of suitable configurations include conventional configurations for bone screw cutting edges. Different configurations may be appropriate for orthopedic screws intended for use in different tissues and/or applications. For example, an orthopedic screw intended for use in fracture fixation in the foot and/or ankle may have one cutting edge configuration while an orthopedic screw intended for us in fracture fixation in the upper extremities may have another, different cutting edge configuration. Orthopedic screws intended for other uses, such as spinal or trauma applications, may have yet other cutting edge configurations.

The body 1160 extends between the head 1120 and the tip 1140 along the longitudinal axis 1108 of the orthopedic screw 1000. As best illustrated in FIG. 2, the body 1160 has an outer surface 1162 and defines a circumferential recess 1164 in the outer surface 1162. The circumferential recess 1164 extends entirely around the longitudinal axis 1008 of the orthopedic screw 1000. The body 1160 defines a proximal recess wall 1166, a distal recess wall 1168, and a recess floor 1170. The circumferential recess 1164 is bounded by the proximal recess wall 1166, distal recess wall 1168, and recess floor 1170. Each of the proximal recess wall 1166, distal recess wall 1168, and recess floor 1170 can have any suitable configuration, and a skilled artisan will be able to select an appropriate configuration for each of the proximal recess wall, distal recess wall, and recess floor in an orthopedic screw according to a particular embodiment based on various considerations, including the nature of the outer body member and any method used to associate the outer body member with the inner core member of the orthopedic screw. As best illustrated in FIG. 2, in this example, the recess floor 1170 is configured such that a sectional plane that includes the longitudinal axis 1008 of the orthopedic screw 1000 also contains opposing portions of the recess floor 1170. Also in this example, the proximal recess wall 1166 is configured such that a sectional plane that includes the longitudinal axis 1008 of the orthopedic screw 1000 includes a portion of the proximal recess wall that extends along a line that is transverse to the longitudinal axis 1008 of the orthopedic screw 1000. Similarly, the distal recess wall 1168 is configured such that a sectional plane that includes the longitudinal axis 1008 of the orthopedic screw 1000 includes a portion of the distal recess wall that extends along a line that is transverse to the longitudinal axis 1008 of the orthopedic screw 1000. The proximal recess wall 1166 and distal recess wall 1168 are disposed at opposing angles to each other with respect to the longitudinal axis 1008 of the orthopedic screw. That is, as best illustrated in FIG. 2, the proximal recess wall 1166 extends from the recess floor 1170 and radially outward toward the proximal end 1102 of the orthopedic screw 1000, while the distal recess wall 1168 extends from the recess floor 1170 radially outward toward the distal end 1104 of the orthopedic screw 1000. This structural arrangement of the proximal recess wall 1166, distal recess wall 1168, recess floor 1170, and the circumferential recess 1164 is considered advantageous at least because it provides surfaces, as the proximal 1166 and distal 1168 recess walls, against which the outer body member 1200 can be positioned and sealed during an injection or other molding process in which the outer body member 1200 is formed in the circumferential recess 1164 of the inner core member 1100. Also, this structural configuration provides a substantially continuous outer surface across the contact interfaces 1250, 1252 between the inner core member 1100 and outer body member 1200, as described in more detail below.

As best illustrated in FIG. 2, the inner core member 1100 has a first outer diameter 1180 at the head 1120, a second outer diameter 1182 at the tip 1140, and a third outer diameter 1184 at the circumferential recess 1164 of the body 1106. The first outer diameter 1180 is greater than both the second outer diameter 1182 and the third outer diameter 1184. Also, the second outer diameter 1182 is greater than the third outer diameter 1184.

The outer body member 1200 has a proximal end 1202, a distal end 1204, and a body 1206 extending between the proximal end 1202 and the distal end 1204. As best illustrated in FIG. 2, the outer body member 1200 defines a lumen 1208 extending between the proximal end 1202 and the distal end 1204. The body 1106 of the inner core member 1100 is disposed within the lumen 1208 of the outer body member 1200. Also, the proximal end 1202 of the outer body member 1200 defines a proximal engaging surface 1210 that is in contact interface with the proximal recess wall 1166 of the inner core member 1100. Together, the proximal engaging surface 1210 and the proximal recess wall 1166 form a proximal circumferential contact interface 1250 between inner core member 1100 and the outer body member 1200. Similarly, the distal end 1204 of the outer body member 1200 defines a distal engaging surface 1212 that is in contact interface with the distal recess wall 1168 of the inner core member 1100. Together, the distal engaging surface 1212 and the distal recess wall 1168 form a distal circumferential contact interface 1252 between inner core member 1100 and the outer body member 1200. The outer body member 1200 has an internal surface 1214 that is in contact interface with the recess floor 1170 of the inner core member 1100. For each of the proximal engaging surface 1210, distal engaging surface 1212, and the internal surface 1214, the surface of the outer body member 1200 is advantageously in continuous or substantially continuous contact interface with the respective structure of the circumferential recess 1164 of the inner core member 1100.

The outer body member 1200 defines an outer body member external thread 1216. In this example, as best illustrated in FIG. 2, the outer body member external thread 1216 extends along substantially the entire axial length of the outer body member 1200.

The outer body member external thread 1216 can have any suitable structural configuration, and a skilled artisan will be able to select an appropriate configuration for the external thread in an orthopedic screw according to a particular embodiment based on various considerations, including the nature of any tissue with which the orthopedic screw is intended to be used. In one example embodiment, not illustrated, the outer body member external thread 1216 defines one or more sawing teeth, the inclusion of sawing teeth in the outer body member external thread 1216 is considered particularly advantageous at least because these structures provide additional cutting functionality to the orthopedic screw.

Figure 3:
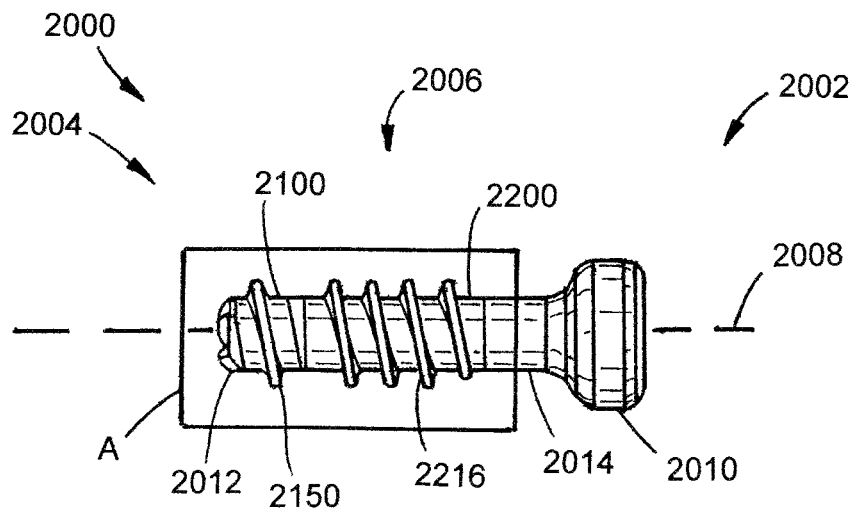
FIG. 3 is a side view of a second example orthopedic screw.
Figure 4:
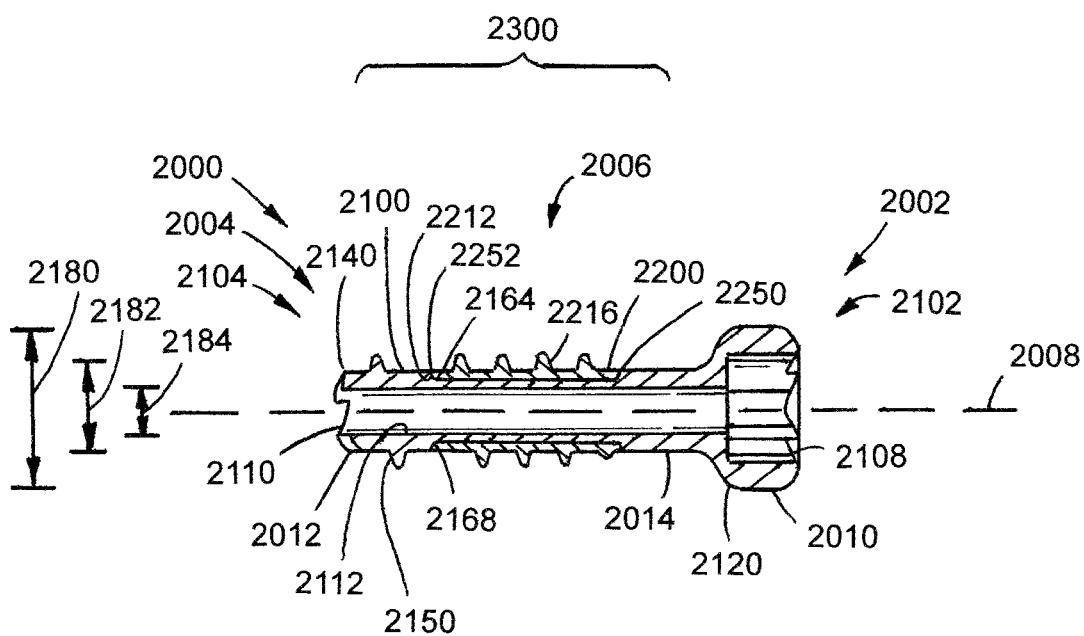
FIG. 4 is longitudinal cross-sectional view of the second example orthopedic screw.
Figure 5:
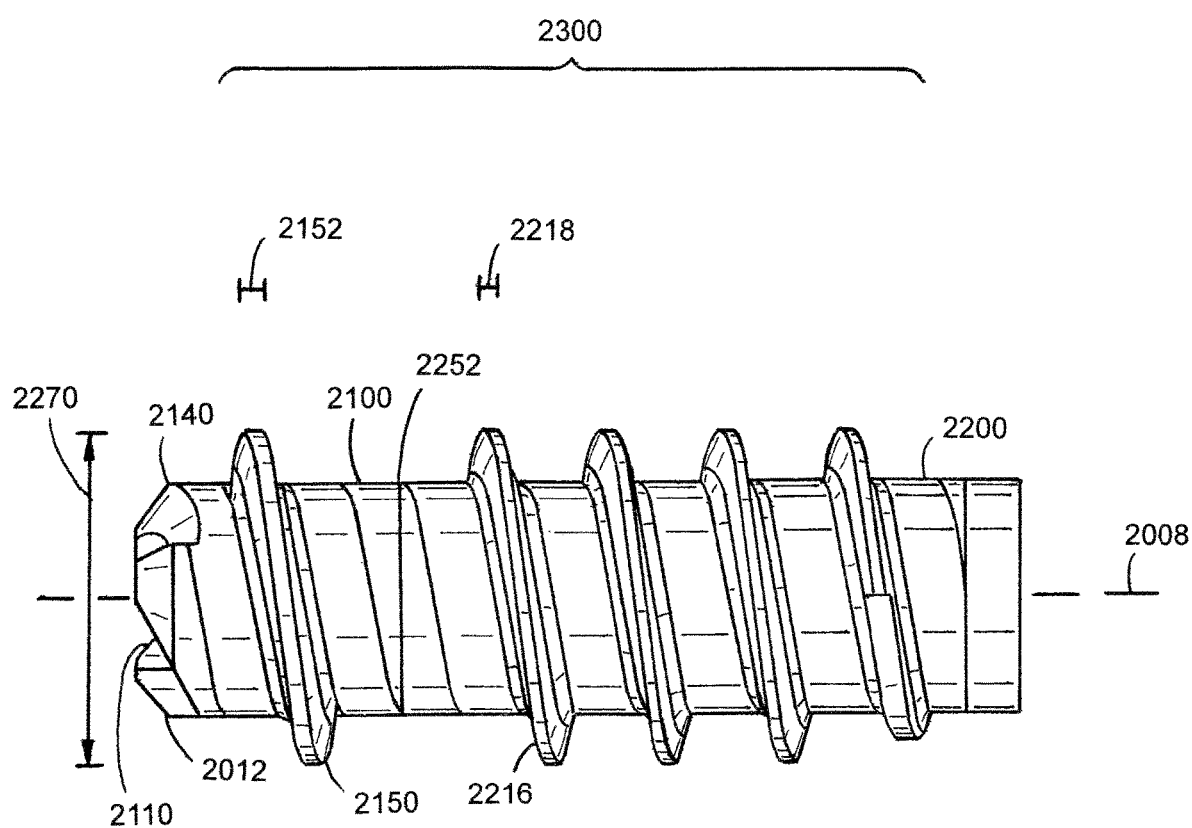
FIG. 5 is a magnified view of Area A of FIG. 3.

FIGS. 3, 4 and 5 illustrate a second example orthopedic screw 2000. The orthopedic screw 2000 is identical to the orthopedic screw 1000 described above and illustrated in FIGS. 1 and 2, except as detailed below. Thus, orthopedic screw 2000 has a proximal end 2002, a distal end 2004, and a body 2006 extending between the proximal end 2002 and the distal end 2004 along a longitudinal axis 2008. The orthopedic screw 2000 includes a head portion 2010 located at the proximal end 2002, a tip portion 2012 located at the distal end 2004, and a shaft 2014 extending between the head portion 2010 and the tip portion 2012 and comprising the body 2006. The orthopedic screw 2000 includes an inner core member 2100 and an outer body member 2200 disposed circumferentially around an axial portion of the inner core member 2100. The outer body member 2200 defines an outer body member external thread 2216. The inner core member 2100 defines a lumen 2112 extending between a proximal opening 2108 and a distal opening 2110. As best illustrated in FIG. 4, the inner core member 2100 has a first outer diameter 2180 at the head 2120, a second outer diameter 2182 at the tip 2140, and a third outer diameter 2184 at the circumferential recess 2164 of the body 2106. The first outer diameter 2180 is greater than both the second outer diameter 2182 and the third outer diameter 2184. Also, the second outer diameter 2182 is greater than the third outer diameter 2184.

In this example, the inner core member 2100 defines an inner core member external thread 2150. The inner core member external thread 2150 can have any suitable structural configuration, and a skilled artisan will be able to select an appropriate configuration for the external thread in an orthopedic screw according to a particular embodiment based on various considerations, including the nature of any tissue with which the orthopedic screw is intended to be used. In this example, the inner core member external thread 2150 is a self-tapping thread. This is considered advantageous at least because inclusion of a self-tapping thread as the inner core member external thread 2150 facilitates and simplifies implantation of the orthopedic screw 2000.

It is considered advantageous for the inner core member external thread 2150 to have a structure that places the inner core member external thread 2150 on the same helical plane as that of the outer body member external thread 2216. The inner core member external thread 2150 can include approximately less than one, one, or more than one rotations around the longitudinal axis 2008 of the orthopedic screw 2000. Also, as best illustrated in FIG. 5, it is considered advantageous to have the entire distal circumferential contact interface 2252 between the distal recess wall 2168 of the inner core member 2100 and the distal engaging surface 2212 of the outer body member 2200 free of any portion of a thread, including both the inner core member external thread 2150 and the outer body member external thread 2216. As such, in this example, the inner core member external thread 2150 and the outer body member external thread 2216 cooperatively define an interrupted thread 2300. The interrupted thread 2300 extends along a helical plane that spans the outer body member 2200 and the tip 2140 of the inner core member 2100, with an interruption in the interrupted thread 2300 at the distal circumferential contact interface 2252 between the proximal recess wall 2166 of the inner core member 2100 and the proximal engaging surface 2210 of the outer body member 2200. Thus, the entire distal circumferential contact interface 2252 between the distal recess wall 2168 of the inner core member 2100 and the distal engaging surface 2212 of the outer body member 2200 is free of any portion of the interrupted thread 2300, including the outer body member external thread 2216 and the inner core member external thread 2150. This structural arrangement is considered advantageous at least because it provides the distal circumferential contact interface 2252 as a defined sealing surface for injection molding of the outer body member 2200 over the inner core member 2100 while avoiding the challenges of a hybrid thread that traverses the distal circumferential contact interface 2252.

The outer body member external thread 2216 and the inner core member external thread 2150 can have the same or different thread properties, such as outer diameter and flage width. In this example, however, the inner core member external thread 2150 and the outer body member external thread 2216 have the same outer diameter 2270 but have different flange widths. As best illustrated in FIG. 5, the inner core member external thread 2150 has a first flange width 2152 and the outer body member external thread 2216 has a second flange width 2218. The first flange width 2152 is different from the second flange width 2218. In this example, the first flange width 2152 is greater than the second flange width 2218. This is considered advantageous at least because, during implantation, it enables the inner core member external thread 2150 to cut a path through tissue that reduces friction between the outer body member external thread 2216 and the tissue once the outer body member external thread 2216 engages the tissue. During use, this requires less insertion torque which enables the development of relatively longer orthopedic screws.

A variety of different flange widths can be used in an orthopedic screw according to a particular embodiment, and a skilled artisan will be able to select an appropriate pairing of different flange widths based on various considerations, including the nature of the tissue with which the orthopedic screw is intended to be used, the overall length of the orthopedic screw, and any desired limitations on insertion torque for the orthopedic screw. A first flange width that is between about 5 times the second flange and about 1.001 times the second flange width is considered advantageous at least because the different flange widths in this range are believed to provide desirable handling and performance properties for an orthopedic screw and are believed to allow for the development of orthopedic screws of considerable and useful lengths. A first flange width that is between about 3 times the second flange and about 1.01 times the second flange width is considered advantageous at least because the different flange widths in this range are believed to provide desirable handling and performance properties for an orthopedic screw and are believed to allow for the development of orthopedic screws of considerable and useful lengths. A first flange width that is between about 1.1 times the second flange and about 1.01 times the second flange width is considered advantageous at least because the different flange widths in this range are believed to provide desirable handling and performance properties for an orthopedic screw and are believed to allow for the development of orthopedic screws of considerable and useful lengths. A first flange width that is about 1.01 times the second flange is considered advantageous at least because these different flange widths are believed to provide desirable handling and performance properties for an orthopedic screw and are believed to allow for the development of orthopedic screws of considerable and useful lengths. A first flange width can be greater than about 1.01 times the second flange width. A first flange width that is between about 1.01 times the second flange and about 1.001 times the second flange width is considered advantageous at least because the different flange widths in this range are believed to provide desirable handling and performance properties for an orthopedic screw and are believed to allow for the development of orthopedic screws of considerable and useful lengths.

Figure 6:
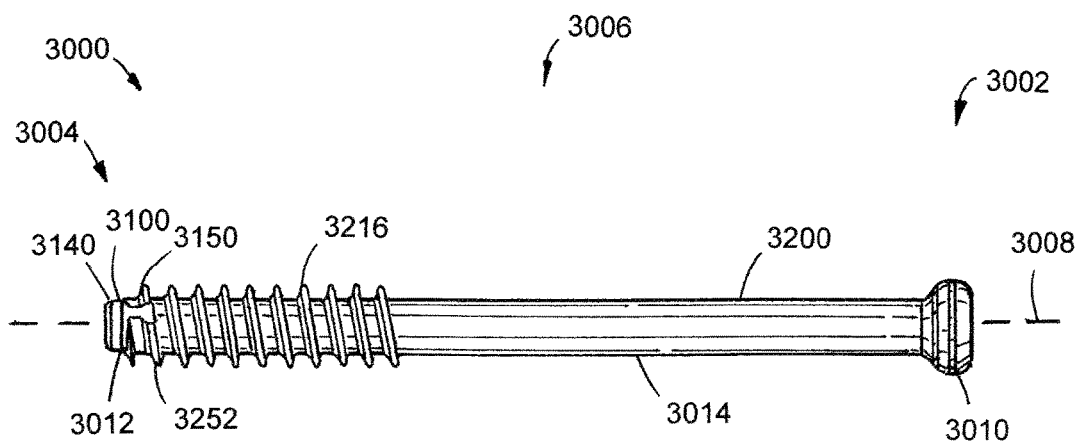
FIG. 6 is a side view of a third example orthopedic screw.
Figure 7:
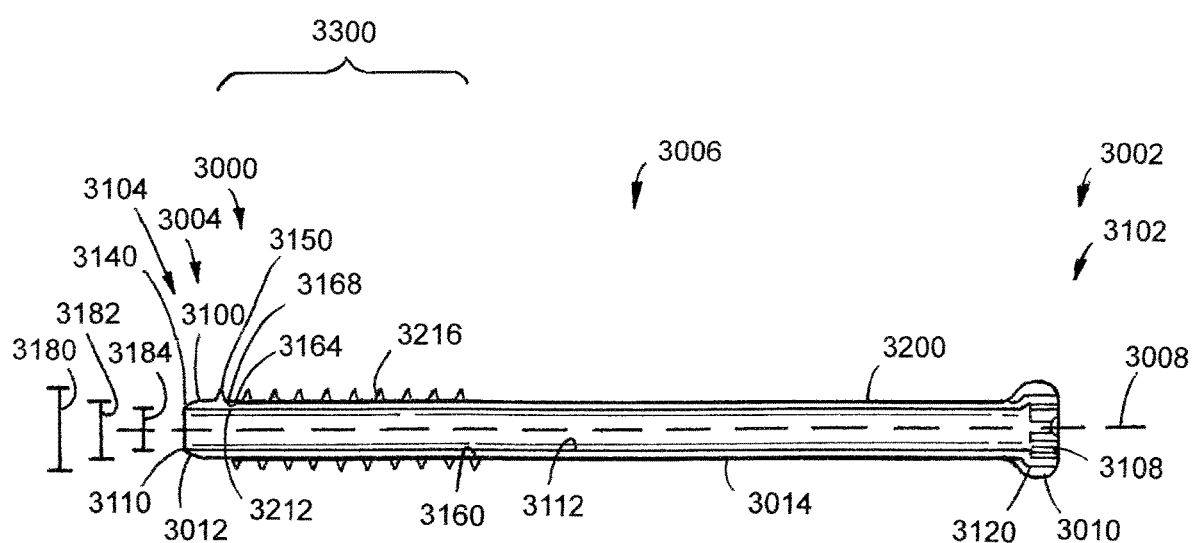
FIG. 7 is longitudinal cross-sectional view of the third example orthopedic screw.
Figure 8:
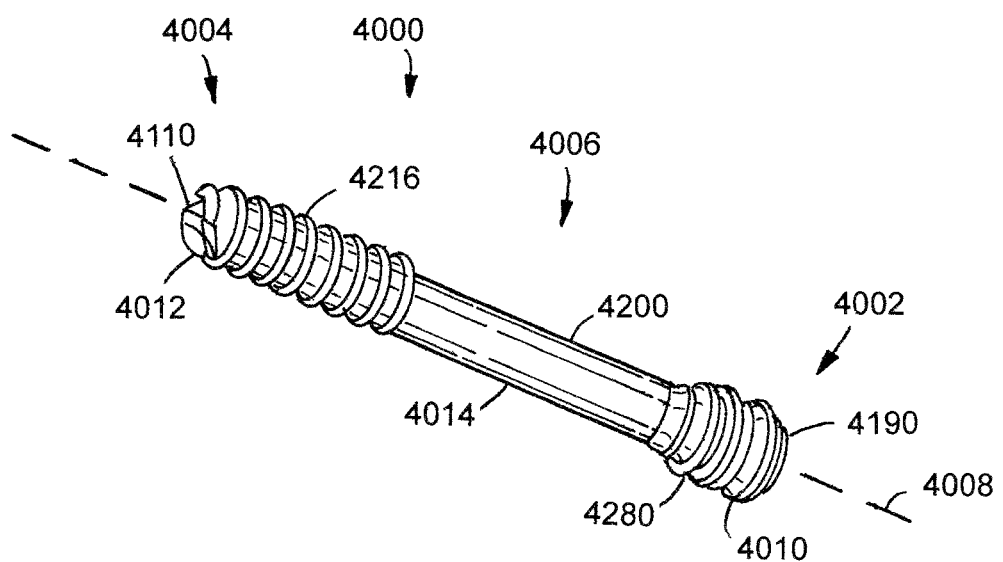
FIG. 8 is a perspective view of a fourth example orthopedic screw.

FIGS. 6 and 7 illustrate a third example orthopedic screw 3000. The orthopedic screw 3000 is similar to the orthopedic screw 2000 described above and illustrated in FIGS. 3, 4, and 5, except as detailed below. Thus, orthopedic screw 3000 has a proximal end 3002, a distal end 3004, and a body 3006 extending between the proximal end 3002 and the distal end 3004 along a longitudinal axis 3008. The orthopedic screw 3000 includes a head portion 3010 located at the proximal end 3002, a tip portion 3012 located at the distal end 3004, and a shaft 3014 extending between the head portion 3010 and the tip portion 3012 and comprising the body 3006. The orthopedic screw 3000 includes an inner core member 3100 and an outer body member 3200 disposed circumferentially around a portion of the inner core member 3100. The outer body member 3200 defines an outer body member external thread 3216. The inner core member 3100 defines a lumen 3112 extending between a proximal opening 3108 and a distal opening 3110. As best illustrated in FIG. 7, the inner core member 3100 has a first outer diameter 3180 at the head 3120, a second outer diameter 3182 at the tip 3140, and a third outer diameter 3184 at the circumferential recess 3164 of the body 3106. The first outer diameter 3180 is greater than both the second outer diameter 3182 and the third outer diameter 3184. Also, the second outer diameter 3182 is greater than the third outer diameter 3184.

Inner core member 3100 defines an inner core member external thread 3150 that lies on the same helical plane as that of the outer body member external thread 3216. As best illustrated in FIG. 6, inner core member external thread 3150 extends less than one rotation around the longitudinal axis 3008 of the orthopedic screw 3000. Also, the entire distal circumferential contact interface 3252 between the distal recess wall 3168 of the inner core member 3100 and the distal engaging surface 3212 of the outer body member 3200 is free of any portion of both the inner core member external thread 3150 and the outer body member external thread 3216 such that the inner core member external thread 3150 and the outer body member external thread 3216 cooperatively define an interrupted thread 3300. The interrupted thread 3300 extends along a helical plane that spans a portion of the axial length of the outer body member 3200 and the tip 3140 of the inner core member 3100, with an interruption in the interrupted thread 3300 at the distal circumferential contact interface 3252 between the proximal recess wall 3166 of the inner core member 3100 and the proximal engaging surface 3210 of the outer body member 3200.

In this example, the outer body member 3200 extends along and is disposed circumferentially around the body 3160 and head 3120 of of the inner core member 3100.

Furthermore, in this example, the outer body member external thread 3216 extends along only a portion of the axial length of the of the outer body member 3200. As a result, a portion of the body 3106 of the inner core member 3100 is circumferentially surrounded by the outer body member 3200 but does not include any thread structure. As a result, a portion of the shaft 3014 of the orthopedic screw 3000 between the outer body member external thread 3216 and the head portion 3010 of the orthopedic screw 3000 lacks an external thread structure. This structural arrangement is considered advantageous for orthopedic screws of moderate length, such as orthopedic screws having a length between about 4 mm and about 6 mm. It is noted, though, that this structural arrangement can be used in an orthopedic screw according to an embodiment that is longer or shorter than this range of screw lengths. A partial length outer body member external thread can extend along any suitable portion of the axial length of the outer body member, and a skilled artisan will be able to select an appropriate portion of the axial length of the outer body member of an orthopedic screw according to a particular embodiment based on various considerations, including the overall axial length of the orthopedic screw and the nature of the tissue with which the orthopedic screw is intended to be used. A portion of the axial length of the outer body member that is between about 25% and about 90% of the axial length of the outer body member is considered advantageous at least because the axial lengths in this range are believed to provide desirable handling and performance properties for an orthopedic screw and are believed to allow for the development of orthopedic screws of considerable and useful lengths. A portion of the axial length of the outer body member that is between about 30% and about 75% of the axial length of the outer body member is considered advantageous at least because the axial lengths in this range are believed to provide desirable handling and performance properties for an orthopedic screw and are believed to allow for the development of orthopedic screws of considerable and useful lengths. A portion of the axial length of the outer body member that is between about 33% and about 50% of the axial length of the outer body member is considered advantageous at least because the axial lengths in this range are believed to provide desirable handling and performance properties for an orthopedic screw and are believed to allow for the development of orthopedic screws of considerable and useful lengths. A portion of the axial length of the outer body member that is about 33% of the axial length of the outer body member is considered advantageous at least because this axial length is believed to provide desirable handling and performance properties for an orthopedic screw and are believed to allow for the development of orthopedic screws of considerable and useful lengths. It is noted that an outer body member external thread can extend along the full axial length, or substantially the full axial length, of the outer body member in some embodiments.

Figure 9:
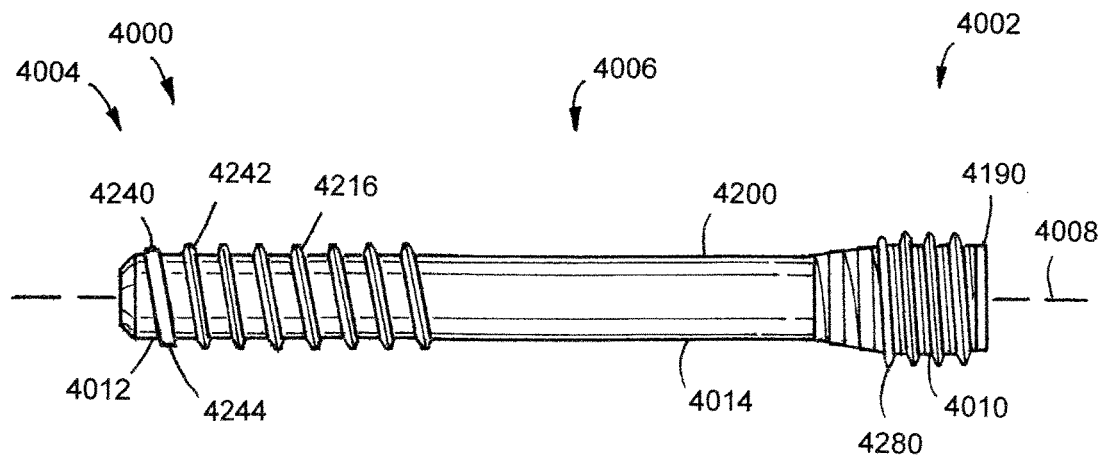
FIG. 9 is a side view of the fourth example orthopedic screw.
Figure 10:
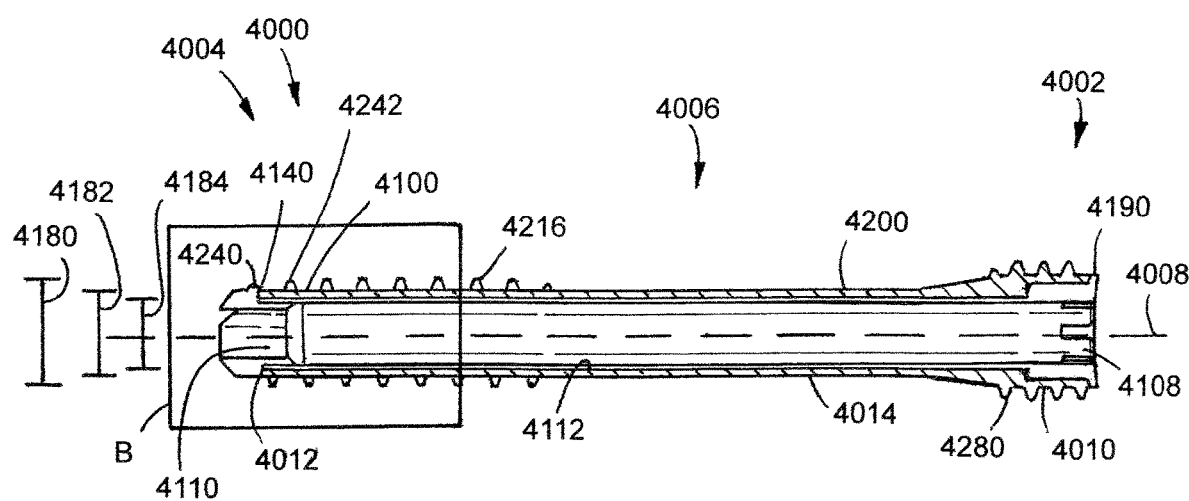
FIG. 10 is longitudinal cross-sectional view of the fourth example orthopedic screw.

FIGS. 8, 9, 10, 11, 12, 13, 14, and 15 illustrate a fourth example orthopedic screw 4000. The orthopedic screw 4000 is similar to the orthopedic screw 3000 described above and illustrated in FIGS. 6 and 7, except as detailed below. Thus, orthopedic screw 4000 has a proximal end 4002, a distal end 4004, and a body 4006 extending between the proximal end 4002 and the distal end 4004 along a longitudinal axis 4008. The orthopedic screw 4000 includes a head portion 4010 located at the proximal end 4002, a tip portion 4012 located at the distal end 4004, and a shaft 4014 extending between the head portion 4010 and the tip portion 4012 and comprising the body 4006. The orthopedic screw 4000 includes an inner core member 4100 and an outer body member 4200 disposed circumferentially around a portion of the inner core member 4100. The outer body member 4200 defines an outer body member external thread 4216. The inner core member 4100 defines a lumen 4112 extending between a proximal opening 4108 and a distal opening 4110. As best illustrated in FIG. 10, the inner core member 4100 has a first outer diameter 4180 at the head 4120, a second outer diameter 4182 at the tip 4140, and a third outer diameter 4184 at the circumferential recess 4164 of the body 4106. The first outer diameter 4180 is greater than both the second outer diameter 4182 and the third outer diameter 4184. Also, the second outer diameter 4182 is greater than the third outer diameter 4184.

The outer body member external thread 4216 extends along only a portion of the axial length of the of the outer body member 4200. As a result, a portion of the body 4106 of the inner core member 4100 is circumferentially surrounded by the outer body member 4200 but does not include any thread structure. As a result, a portion of the shaft 4014 of the orthopedic screw 4000 between the outer body member external thread 4216 and the head portion 4010 of the orthopedic screw 4000 lacks an external thread structure.

Figure 12:
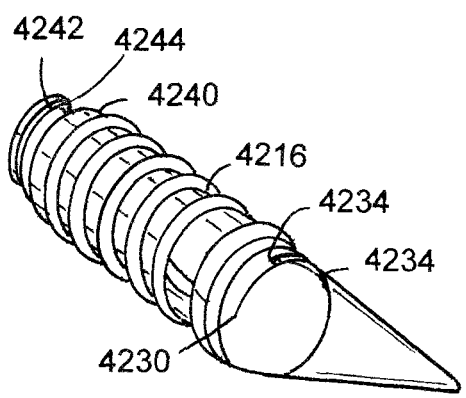
FIG. 12 is a partial perspective view of the fourth example orthopedic screw.
Figure 13:
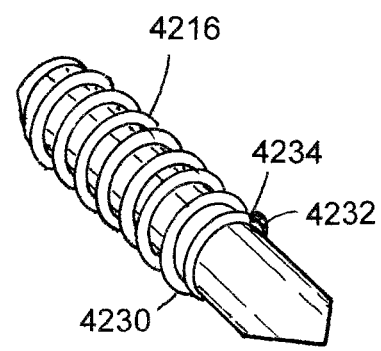
FIG. 13 is a partial perspective view of the fourth example orthopedic screw. The orthopedic screw is rotated 180° about its longitudinal axis in comparison to the view illustrated in FIG. 13.
Figure 14:
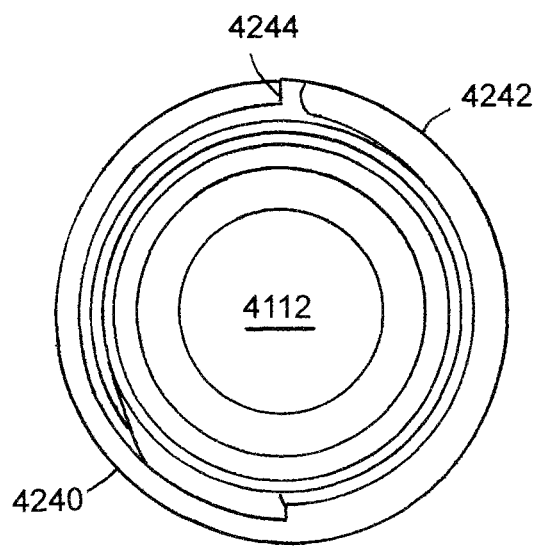
FIG. 14 is an end view of the fourth example orthopedic screw.

As best illustrated in FIGS. 12, 13, and 14, the outer body member external thread 4216 has a first proximal thread height 4230, a second proximal thread height 4232 that is greater than the first proximal thread height 4230, and a proximal thread shoulder 4234 that transitions the outer body member external thread 4216 from the first proximal thread height 4230 to the second proximal thread height 4243. Similarly, the outer body member external thread 4216 has a first distal thread height 4240, a second distal thread height 4242 that is greater than the first distal thread height 4240, and a distal thread should 4244 that transitions the outer body member external thread 4216 from the first proximal thread height 4240 to the second proximal thread height 4242. Inclusion of these different heights on the outer body member external thread 4216 is considered advantageous at least because it provides a thread that cuts in two steps. Overall, the outer body member external thread 4216 in this embodiment has a discontinuous portion that allows the cutting geometry of the outer body member external thread 4216 to fully face the bone into which the orthopedic screw 4000 is being drive, enabling the orthopedic screw 4000 to realize more of its cutting potential.

While the illustrated example includes multiple thread heights at both the proximal and distal ends of the outer body member external thread 4216, it is understood that inclusion of multiple thread heights at only one of the proximal and distal ends of the outer body member external thread 4216 is within the scope of embodiments.

Figure 11:
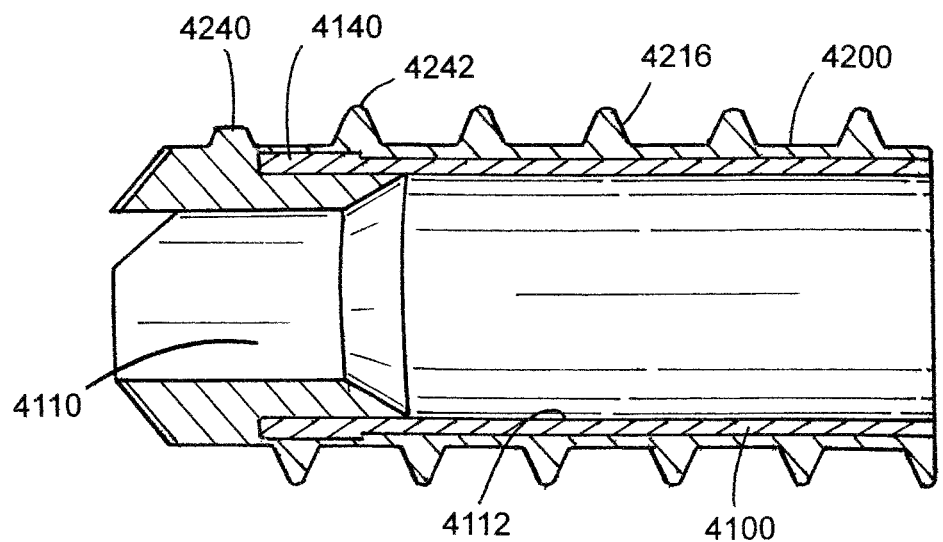
FIG. 11 is a magnified view of Area B of FIG. 10.

In this example, inner core member 4100 lacks an external thread. Rather, the outer body member 4200 extends along and is disposed circumferentially around the body 4160 and tip 4140 of the inner core member 4100. Indeed, as best illustrated in FIGS. 10 and 11, the outer body member 4200 extends axially beyond the tip 4140 of the inner core member 4100. Thus, in contrast to the embodiments described above, orthopedic screw 4000 does not define an interrupted thread on the body 4006 and tip portion 4012 of the orthopedic screw 4000. Rather, the orthopedic screw 4000 includes a continuous thread, as outer body member external thread 3216, that extends along an axial portion of the body 4006 and tip portion 4012 of the orthopedic screw 4000. Also in this embodiment, as a result of the outer body member 4200 extending axially beyond the top 4140 of the inner core member 4200, the outer body member 4200 defines the distal end 4004 of the orthopedic screw 4000. Also, as best illustrated in FIG. 10, outer body member 4200 defines a distal tip inner diameter 4185 that is less than the inner diameter 4187 of the inner core member 4100. This structural arrangement is considered advantageous at least because it provides a relatively smaller leading guide diameter at the distal end 4004 of the orthopedic screw 4000, which can facilitate placement of the orthopedic screw 4000 over a previously-positioned wire. This can be particularly advantageous for relatively long orthopedic screws (e.g. screws with a total axial length of between about 6 mm and about 8 mm, or larger than 8 mm).

Also in this embodiment, the inner core member 4100 defines a circumferential flange 4190 on the proximal end 4102. Inclusion of the circumferential flange 4190 is considered advantageous at least because it provides a surface against which the outer body member 4200 can be positioned and sealed during an injection or other molding process in which the outer body member 4200 is formed circumferentially about the inner core member 4100. As best illustrated in FIGS. 9 and 10, the outer body member 4200 in this example extends to and against, but is not disposed over, the circumferential flange 4190.

Figure 15:
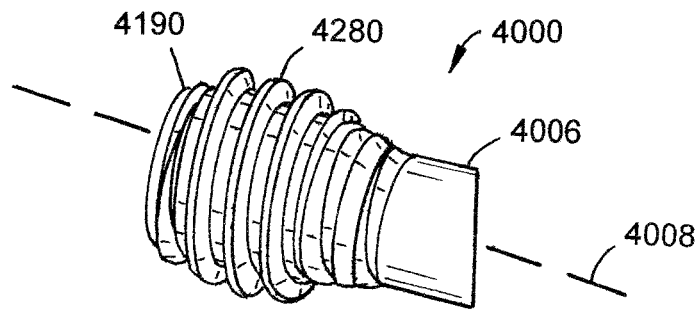
FIG. 15 is a partial perspective view of the fourth example orthopedic screw.

Also in this embodiment, outer body member 4200 defines a second outer body member external thread 4280 on the head portion of the orthopedic screw 4000. As best illustrated in FIG. 10, the second outer body member external thread 4280 is positioned over the head 4120 and a portion of the body 4106 of the inner core member 4100. Furthermore, as best illustrated in FIGS. 9 and 15, the second outer body member external thread 4280 includes structural features that prepare tissue, such as bone, into which the orthopedic screw 4000 is being implanted for the larger thread diameter of the second outer body member external thread 4280 as compared to the smaller thread diameter of the outer body member external thread 4216 located on the body 4006 and tip portion 4012 of the orthopedic screw 4000. In this example, the second outer body member external thread 4280 includes a uniformly increasing thread diameter with multiple cutting steps, or thread shoulders, that transition the second outer body member external thread 4280 from one thread diameter to another along the helical plane of the thread.

Figure 16:
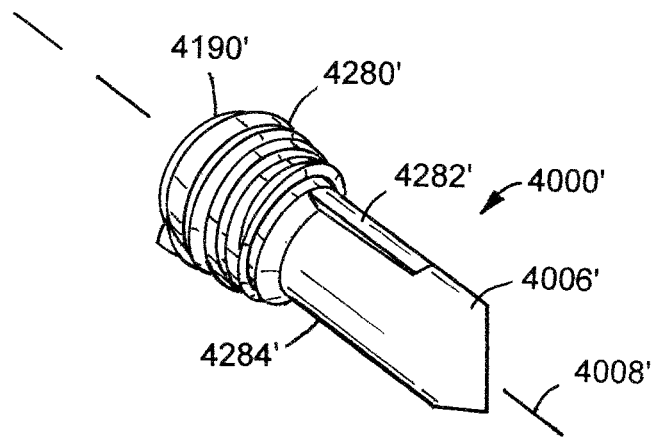
FIG. 16 is a partial perspective view of an alternative orthopedic screw.
Figure 17:
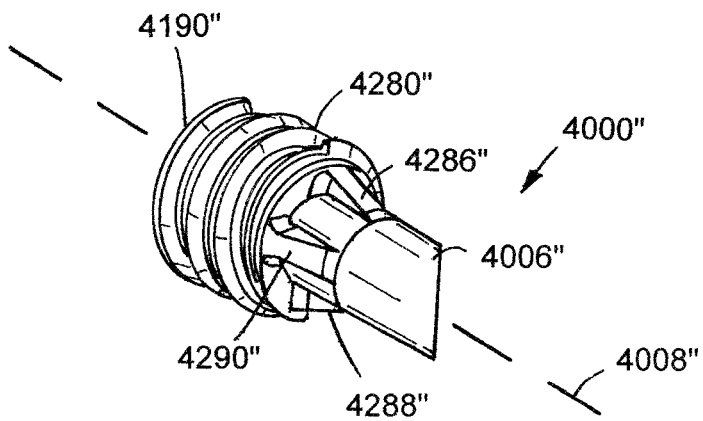
FIG. 17 is a partial perspective view of another alternative example orthopedic screw.

FIG. 16 illustrates a portion of the body 4006' and head portion 4010' of an alternative orthopedic screw 4000'. The alternative orthopedic screw 4000' includes a second outer body member external thread 4280' and first 4282' and second 4284' cutting blades that extend from the body 4006' to the second outer body member external thread 4280'. The inclusion of cutting blades is considered advantageous at least because it facilitates reaming. If included, any suitable number of cutting blades can be included, and the illustrated first 4280' and second 4282' cutting blades represent one example structure. Furthermore, if included, the cutting blades can be arranged in any suitable manner. In the illustrated example, the first 4282' and second 4284' cutting blades are positioned opposite each other with respect to the longitudinal axis 4008' of the orthopedic screw 4000'. FIG. 17 illustrates a portion of the body 4006" and head portion 4010" of another alternative orthopedic screw 4000". This alternative orthopedic screw 4000" includes first 4286', second 4288', third 4290", and fourth (not visible in FIG. 17) cutting blades that extend from the body 4006" to the second outer body member external thread 4280". In this example, the first 4286" and second 4288" cutting blades are positioned opposite each other with respect to the longitudinal axis 4008" of the orthopedic screw 4000". Similarly, the third 4290" and fourth cutting blades are positioned opposite each other with respect to the longitudinal axis 4008" of the orthopedic screw 4000".

Figure 18A:
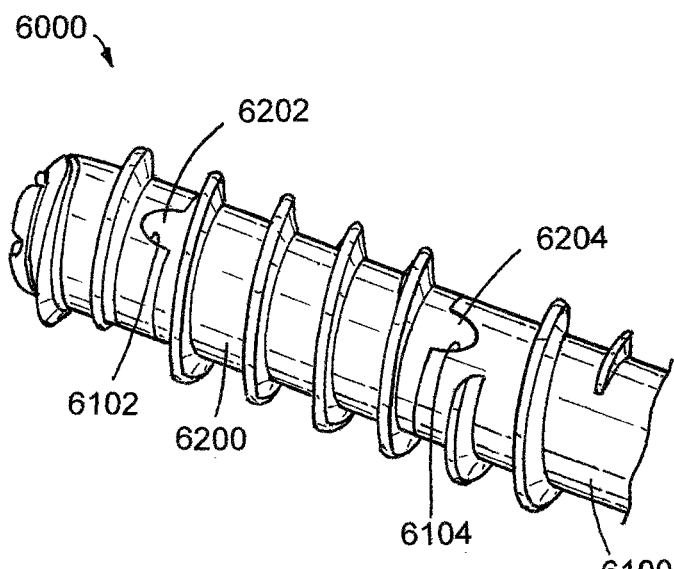
FIG. 18A is a perspective view of another example orthopedic screw.

FIG. 18A illustrates another example orthopedic screw 6000. In this example, the outer body member 6200 defines first 6202 and second 6204 axially-extending projections that are received by first 6102 and second 6104 recesses defined by the inner core member 6100. The inclusion of axially-extending projections 6202, 6204 and recesses 6102, 6104 is considered advantageous at least because the structural interface between these elements provides additional contact surface area between the inner core member 6100 and outer body member 6200. While the illustrated orthopedic screw 6000 includes two axially extending projections 6202, 6204 and two corresponding recesses 6102, 6104, it is noted that an orthopedic screw according to a particular embodiment can include any suitable number of axially-extending projections and corresponding recesses. A skilled artisan will be able to select a suitable number of axially-extending projections and corresponding recesses for an orthopedic screw according to a particular embodiment based on a variety of considerations, including any desired contact surface area between the inner core member and outer body member elements of the particular orthopedic screw. Examples of suitable numbers of axially-extending projections and corresponding recesses include one, at least one, more than one, two, three, a plurality, four, five, six, seven, eight, nine, ten, eleven, twelve, and more than twelve.

Figure 18B:
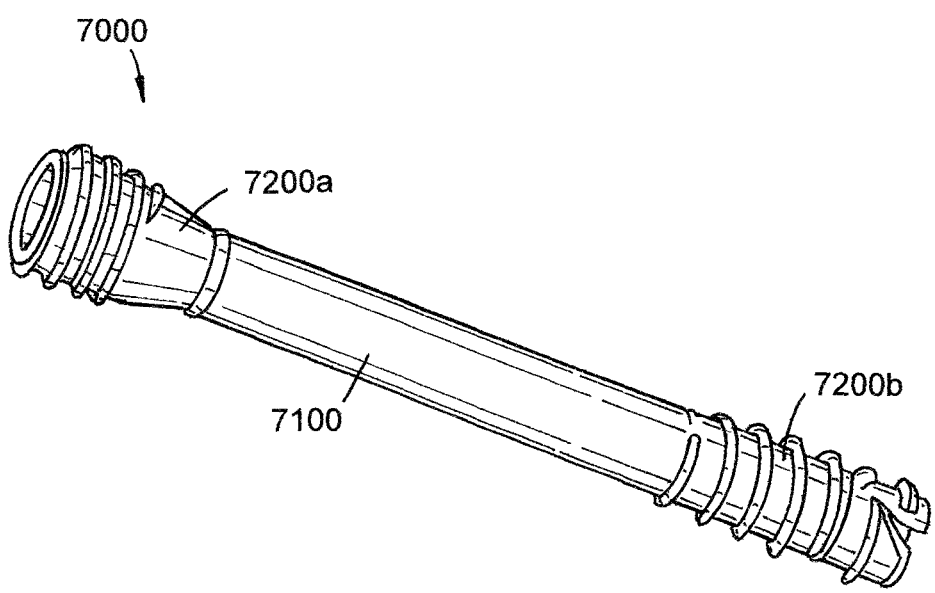
FIG. 18B is a perspective view of another example orthopedic screw.

FIG. 18B illustrates another example orthopedic screw 7000. In this example, orthopedic screw 7000 includes first 7200a and second 7200b outer body members, each of which is circumferentially disposed around and contacting inner core member 7100. While the illustrated orthopedic screw 7000 includes two outer body member 7200a, 7200b, it is noted that an orthopedic screw according to a particular embodiment can include any suitable number of outer body members circumferentially disposed around and contacting the inner core member. A skilled artisan will be able to select a suitable number of outer body members for an orthopedic screw according to a particular embodiment based on a variety of considerations, including any desired separation between proximal, distal, and other structural features for the particular orthopedic screw. Examples of suitable numbers of outer body members include one, at least one, more than one, two, three, a plurality, four, five, six, seven, eight, nine, ten, eleven, twelve, and more than twelve.

In all embodiments, the inner core member can be made of any material suitable for use in medical devices intended for orthopedic use, including use as a long-term implant. Examples of suitable materials include metals, metal alloys, and polymeric materials. Examples of suitable metals include, but are not limited to, Titanium, Magnesium, and other metals. Examples of suitable metal alloys include, but are not limited to, Ti6Al4V, 316 LVM, 1.4441Ti-13Nb-13Zr, Ti-12Mo-6Zr-2Fe, Ti-15Mo-5Zr-3Al, Ti-15Mo, Ti-35Nb-7Zr-5Ta and Ti-29Nb-13Ta-4.6Zr Ti-6Al-7Nb and Ti-15Sn-4Nb-2Ta-0.2Pd Co—Cr—Mo alloys. Examples of suitable polymeric materials include, but are not limited to, polyaryletherketone (PAEK), polyether ether ketone (PEEK), PEEK (90G, 450G, 12, 14), Polyamid, PA66, carbon fiber reinforced polyaryletherketone (CFR PAEK), polyethere ketone ketone (PEKK), carbon fiber reinforced polyether ketone ketone (CFR PEKK), carbon fiber reinforced polyether ether ketone (CFR PEEK), CFR PEEK (90G CA30, 90G CA20, 450G CA30, 450G CA20, I2 CF20, I2 CF30, I4 CF30, I4 CF20), Polyamid CFR, and PA66 CFR.

In all embodiments, the outer body member can be made of any material suitable for use in medical devices intended for orthopedic use, including use as a long-term implant. Examples of suitable types of materials include, but are not limited to, polymeric materials, blended materials such as carbon fiber reinforced polymers, and other materials. Examples of suitable polymeric materials include, but are not limited to, PAEK, CFR PAEK, PEKK, CFR PEKK, PEEK, CFR-PEEK, PEEK (90G, 450G, I2, I4), Polyamid, and PA66.

Examples of suitable blended materials include, but are not limited to, PEEK-Carbon materials, CFR PAEK, CFR PEKK, CFR PEEK (90G CA30, 90G CA20, 450G CA30, 450G CA20, I2 CF20, I2 CF30, I4 CF30, I4 CF20), Polyamid CFR, PA66 CFR.

It is noted that the materials used in a component of an orthopedic screw according to a particular embodiment can include additives, coatings, fillers, and/or other elements if desired. For example, antibiotics, bioactive glass, silver, copper, or another material that can reduce bacterial colonization of the orthopedic screw following implantation can be included in the material of the inner core member, the outer body member, or both. Furthermore, one or more components of an orthopedic screw according to an embodiment can be treated in a manner that facilitates making of the orthopedic screw, provides structural benefit to the orthopedic screw, or that provides other advantages. For example, in embodiments in which the inner core member comprises a metal, the inventors have determined that anodizing the inner core member in an orthopedic screw according to an embodiment prior to overmolding the inner core member with a suitable material to form the outer body member can be advantageous at least because anodization provides additional surface area on the inner core member to which the material of the outer core member can attach or bond during the overmolding process. Accordingly, an orthopedic screw according to any example described herein, or any other embodiment, can include a metal inner core member that comprises an anodized inner core member. In these embodiments, conventional anodization processes can be used to prepare the metal inner core member prior to overmolding the outer body member to form the orthopedic screw.

The inventors have determined that an orthopedic screw having an inner core member formed of a Titanium alloy, such as Ti6Al4V, and an outer body member formed of CFR PEEK provides desirable characteristics and a favorable balance between manufacturability and strength considerations.

Figure 19:
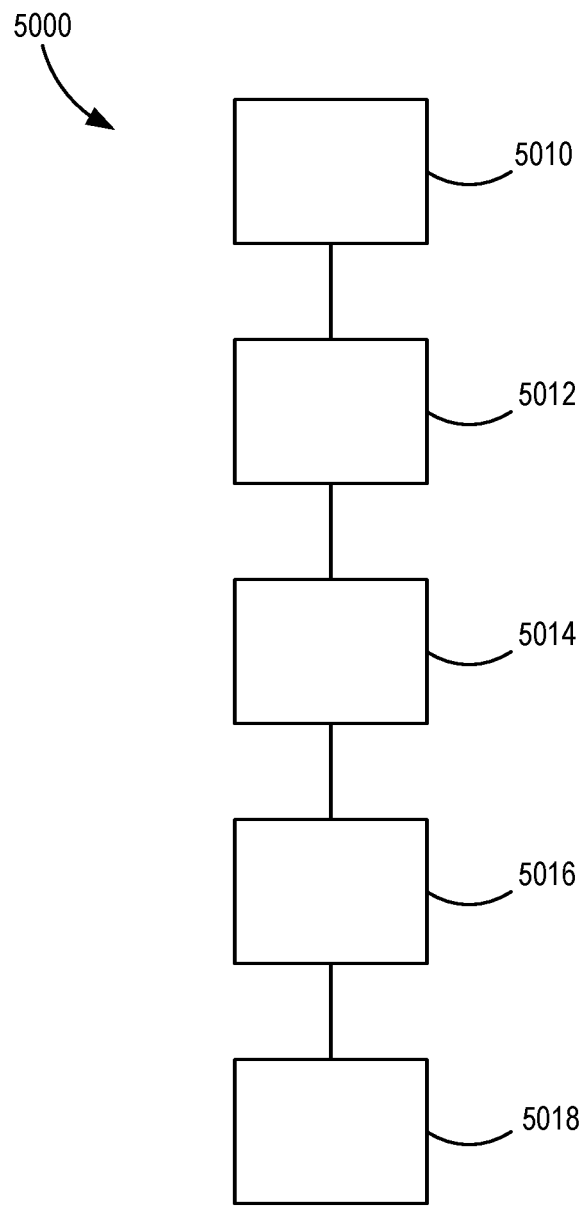
FIG. 19 is a flowchart representation of an example method of manufacturing an orthopedic screw.

FIG. 19 is a schematic representation of a method 5000 of manufacturing a medical device. An initial step 5010 comprises machining the inner core member from a suitable precursor, such as a solid rod or cannula. A next step 5012 comprises placing the inner core member into a suitable mold. A next step 5014 comprises overmolding the inner core member with a suitable material to form the outer body member about the inner core member in accordance with an embodiment of the invention, including any of the examples described and illustrated herein. At this point, a medical device, such as an orthopedic screw, is available. It may be desirable, however, to include additional steps, such as step 5016, which comprises finishing the medical device using suitable techniques or processes. Another additional step 5018 comprises performing one or more surface treatments on the medical device, such as roughening, coating, and the like. An optional step, not illustrated in FIG. 19, includes anodizing the inner core member prior to the step 5014 of overmolding the inner core member with a suitable material to form the outer body member about the inner core member. Inclusion of this step can be advantageous in methods of making an orthopedic screw in which it is desirable to increase the surface area on the inner core member to which the material of the outer core member can attach or bond during the step 5014 of overmolding the inner core member with a suitable material to form the outer body member.

Those with ordinary skill in the art will appreciate that various modifications and alternatives for the described and illustrated examples can be developed in light of the overall teachings of the disclosure, and that the various elements and features of one example described and illustrated herein can be combined with various elements and features of another example without departing from the scope of the invention. Accordingly, the particular examples disclosed herein have been selected by the inventors simly to describe and illustrate examples of the invention are not intended to limit the scope of the invention or its protection, which is to be given the full breadth of the appended claims and any and all equivalents thereof.

We claim:

1. An orthopedic screw, comprising:
an inner core member defining a head having a first outer diameter, a tip having a second outer diameter, the tip defining an inner core member external thread having a first flange width, and a body extending between the head and the tip and having an inner core member outer surface that defines a circumferential recess having a third outer diameter that is less than the first outer diameter and the second outer diameter, the first flange having a first flange first side, a first flange second side, and a first flange crest, the first flange width comprising a thickness of the first flange from the first flange first side to the first flange second side at the first flange crest; and
an outer body member disposed circumferentially around the body and within the circumferential recess, the outer body member having an outer body member outer surface, the outer body member defining an outer body member external thread having a second flange width that is different from the first flange width and that is constant along a majority of an axial length of the outer body member, the second flange having a second flange first side, a second flange second side, and a second flange crest, the second flange width comprising a thickness of the second flange from the second flange first side to the second flange second side at the second flange crest;
wherein the inner core member external thread and the outer body member external thread lie on the same helical plane and cooperatively define an interrupted thread having an interruption that comprises an absence of at least part of a complete revolution of the interrupted thread along each of the inner core member outer surface and the outer body member outer surface adjacent a distal circumferential contact interface between the inner core member and the outer body member;
wherein the outer body member outer surface is flush with a portion of the inner core member outer surface.

2. The orthopedic screw of claim 1, wherein the inner core member defines a distal recess wall that partially bounds the circumferential recess; and
wherein the outer body member defines a distal engaging surface that is in sealing contact with the distal recess wall to form the distal circumferential contact interface between the inner core member and the outer body member.

3. The orthopedic screw of claim 2, wherein the distal engaging surface is free of the outer body member external thread.

4. The orthopedic screw of claim 3, wherein the distal recess wall is free of the inner core member external thread.

5. The orthopedic screw of claim 4, wherein the interruption is disposed at the distal circumferential contact interface between the inner core member and the outer body member.

6. The orthopedic screw of claim 1, wherein the inner core member external thread has an inner core member external thread outer diameter and the outer body member external thread has an outer body member external thread outer diameter that is the same as the inner core member external thread outer diameter.

7. The orthopedic screw of claim 1, wherein the inner core member external thread has an inner core member external thread outer diameter and the outer body member external thread has an outer body member external thread outer diameter that is different from the inner core member external thread outer diameter.

8. The orthopedic screw of claim 1, wherein the first flange width is greater than the second flange width.

9. The orthopedic screw of claim 8, wherein the first flange width is between about 1.1 times the second flange width and about 1.001 times the second flange width.

10. The orthopedic screw of claim 8, wherein the first flange width is between about 1.1 times the second flange width and about 1.01 times the second flange width.

11. The orthopedic screw of claim 8, wherein the first flange width is about 1.01 times the second flange width.

12. The orthopedic screw of claim 8, wherein the first flange width is greater than about 1.01 times the second flange width.

13. The orthopedic screw of claim 1, wherein the inner core member is anodized.

14. The orthopedic screw of claim 13, wherein the inner core member comprises a titanium alloy.

15. The orthopedic screw of claim 14, wherein the outer body member comprises PEEK.

16. The orthopedic screw of claim 14, wherein the outer body member comprises a carbon fiber reinforced polymer.

17. The orthopedic screw of claim 16, wherein the outer body member comprises CFR PEEK.

* * * * *